(12) United States Patent
Mrochen et al.

(10) Patent No.: US 8,282,629 B2
(45) Date of Patent: Oct. 9, 2012

(54) METHOD FOR DETERMINING CONTROL INFORMATION FOR PHOTOREFRACTIVE CORNEAL SURGERY AND METHOD FOR PROVIDING CORRECTION INFORMATION REQUIRED THEREFOR

(75) Inventors: Michael Mrochen, Eglisau (CH); Michael Bueler, Zurich (CH)

(73) Assignee: Wavelight AG, Erlangen (DE)

( * ) Notice: Subject to any disclaimer, the term of this patent is extended or adjusted under 35 U.S.C. 154(b) by 598 days.

(21) Appl. No.: 12/063,754

(22) PCT Filed: Aug. 18, 2006

(86) PCT No.: PCT/EP2006/008176
§ 371 (c)(1),
(2), (4) Date: Jul. 29, 2010

(87) PCT Pub. No.: WO2007/020105
PCT Pub. Date: Feb. 22, 2007

(65) Prior Publication Data
US 2010/0292677 A1 Nov. 18, 2010

(30) Foreign Application Priority Data
Aug. 19, 2005 (DE) .......................... 10 2005 039 367

(51) Int. Cl.
*A61B 18/18* (2006.01)
(52) U.S. Cl. ................................. 606/12; 606/11; 606/5
(58) Field of Classification Search ................ 606/5, 10, 606/11, 12
See application file for complete search history.

(56) References Cited

U.S. PATENT DOCUMENTS
2005/0107775 A1  5/2005 Huang et al.

FOREIGN PATENT DOCUMENTS
DE          10022995 C2    11/2003

OTHER PUBLICATIONS

English-language translation of the Written Opinion of the International Searching Authority (PCT/ISA/237) prepared for international application PCT/EP2006/008176, dated Mar. 4, 2008.*
International Search Report (PCT/EP2006/008176).
W. Wesemann: "Optical and Physiological Limits to Wavefront-controlled Corneal Surgery," Der Ophthalmologe, May 2004, pp. 521-537.

* cited by examiner

*Primary Examiner* — David N Spector
(74) *Attorney, Agent, or Firm* — Haynes and Boone, LLP

(57) ABSTRACT

A method for determining control information for controlling laser radiation irradiated onto the cornea of an eye to be treated photorefractively comprises correcting a corneal ablation profile, obtained by measuring optical properties of the eye, with the aid of correction information, the control information being formed on the basis of the corrected ablation profile thus produced. According to the invention, the correction of the ablation profile is performed in the spatial frequency domain. To this end, the ablation profile is transformed into a spatial frequency spectrum. Corrected amplitude or/and phase values are then determined for various discrete spectral components of the ablation profile on the basis of stored amplitude or/and phase correction information. Subsequently, the spatial frequency spectrum with the amplitude or/and phase corrected spectral components is backtransformed into the geometric spatial domain. The result is the corrected ablation profile. The amplitude and phase correction information in this case respectively represent for a number of spatial frequencies differing at least by the frequency value a predetermined relationship between values of the amplitude or/and phase at the relevant spatial frequency and corrected amplitude or/and phase values at this spatial frequency.

44 Claims, 2 Drawing Sheets

METHOD FOR DETERMINING CONTROL INFORMATION FOR PHOTOREFRACTIVE CORNEAL SURGERY AND METHOD FOR PROVIDING CORRECTION INFORMATION REQUIRED THEREFOR

CROSS REFERENCE

This application was originally filed as Patent Cooperation Treaty Application Number PCT/EP2006/008176 filed Aug. 18, 2006, which claims priority of German Application Number 102005039367.5, filed Aug. 19, 2005.

CROSS-REFERENCE TO RELATED APPLICATION

This application is a United States national phase application of co-pending international patent application number PCT/EP2006/008176, filed Aug. 18, 2006, the disclosure of which is incorporated herein by reference.

BACKGROUND

The invention relates to the technical field of photorefractive corneal surgery in the case of which corneal tissue is processed by means of laser radiation with the goal of remedying, or at least largely reducing, vision defects.

SUMMARY

Laser-based photorefractive corneal surgery is an established method for correcting optical defects of the eye, and thus for improving the patient's sight. In particular, this method can be used to treat defective visions of low order, that is to say, for example, myopia (nearsightedness), hyperopia (farsightedness), astigmatism (cylindrical ametropia), myopic astigmatism and hyperopic astigmatism. A known method of laser corneal surgery is the so-called LASIK (laser in situ keratomileusis). The first step here is for a flap to be cut off from the cornea of the eye to be treated except for a small remnant serving as "hinge". This flap, as it is generally denoted in English among experts, is then folded to the side, whereupon material in the cornea is removed by means of irradiated laser radiation. The material removal is performed substantially in the stroma of the cornea, which is the part of the corneal tissue lying below the corneal epithelium and Bowman's membrane. The tissue removal by means of laser radiation is also denoted as ablation. After the laser treatment, the flap is folded back again onto its original place. Because no open wound remains on the eye, the flap generally heals very quickly again at the corneal tissue lying therebelow.

LASIK is not the sole known method in which corneal tissue is removed by means of laser radiation in order to remedy defective visions. Reference may be made purely by way of example to the so-called photorefractive keratectomy (PRK) as a further representative of one such treatment method. Generally, the invention may be applied in any desired methods of laser corneal surgery in which corneal tissue is ablated by means of laser radiation; there is no intention at all to impose limitation to specific techniques.

A so-called ablation profile must be compiled before the tissue removal. Said profile specifies how much tissue is to be removed at which site of the corneal treatment zone. The ablation profile can therefore be understood as a relief map that fixes the height of the required tissue removal at the various sites of the treatment zone. For example, the ablation profile can be compiled in the form of a two-dimensional matrix whose matrix elements specify the individual height values.

A known technique for determining the ablation profile is based on determining so-called wavefront aberrations of the eye. Optical imaging in the eye is impaired not only by spherical and cylindrical errors, but also by higher order ablations. Wavefront measurements such as, for example, can be carried out with a Hartmann-Shack sensor or a Tscherning sensor also permit the measurement of higher aberrations of the eye. Reference may be made, by way of example, to the article by W. Wesemann: "Optische and physiologische Grenzen der wellenfrontgesteuerten Hornhautchirurgie" ["Optical and physiological limits to wavefront-controlled corneal surgery"] in Der Opthalmologe, 5, 2004, pages 521-537 for further information with regard to the various aberrations of the eye caused by the cornea and the intraocular imaging system, and measurement thereof by means of wavefront sensors. The result of the aberration measurement is a so-called wavefront aberration elevation that respectively specifies a value for the wavefront aberration for various pupil locations. The higher the "elevation" at a site, the larger are the imaging distortions at the relevant pupil location. The wavefront aberration elevation can be approximated mathematically with the aid of Zernike polynomials or Taylor polynomials, for example. The wavefront aberration elevation can be used to derive an associated ablation profile, for example by varying an assumed ablation depth iteratively until the best possible equalization of the travel times of light beams at all locations of the cornea is achieved, and thus the best possible leveling of the wavefront aberration elevation is achieved.

The ablation profiles obtained on the basis of measuring the optical properties of the eye are admittedly affected by the disadvantage that they often have only theoretical validity. In practice, various types of disturbing factors impair the accuracy of the defective vision correction during and after treatment. Thus, for example, peripheral reflection losses during laser removal, postoperative wound healing processes or biomechanical changes in the cornea can lead to deviations between the change in shape of the cornea being targeted (theoretically ideal) and the one actually achieved.

It has therefore been proposed to modify the ablation profile by means of empirically determined correction factors, and to carry out the laser treatment in accordance with the ablation profile thus corrected. A possible mode of procedure in this case is determining the correction factors by averaging the postoperative results of a large number of patients. The uncorrected desired removal profiles of multiplicity of patients obtained by measuring the eye are compared for this purpose with the removal profiles actually resulting after treatment and completed healing. These empirical data are then used as a basis for determining a standard correction matrix of the same size as that of the ablation profile. Each matrix element of the correction matrix denotes a spatially dependent correction factor for the corresponding height value of the ablation matrix. The correction factors of the correction matrix can be specified, for example, as multipliers by which their height values of the removal matrix are to be multiplied element by element in order to arrive at a corrected removal or ablation matrix.

At those sites of the cornea where the real removal (actual value) from the empirical data corresponds well to the planned removal (desired value), the correction factor has the value one, whereas wherever too little is removed as a rule there is a correction factor with a larger value than one.

Correction matrices currently being used in practice can be compared to a parabolic shape. From the center (which corresponds to the middle of the corneal plane), the correction factors increase toward the matrix edges in accordance with the parabolic shape. Thus, when using such correction matrices, the ablation profile is corrected in the geometric spatial region by simply multiplying the matrix elements of the correction matrix by those of the ablation matrix.

It has emerged that the compensation of the disturbing factors that can thus be achieved is frequently unsatisfactory in the case of eyes with greatly irregular structures, in particular.

US 2005/107775 A1 teaches using a correction function with a lowpass characteristic. The lowpass characteristic is intended to compensate postoperative smoothing processes of the corneal epithelium. An ablation profile determined for an eye to be treated is corrected in the geometric spatial domain by iterative convolution until a corrected profile is obtained that corresponds to the convolution product of the original ablation profile with the geometric pulse response function of the lowpass filter. This methodology is particularly expensive in terms of computation.

It is an object of the invention to indicate a way for the patient-related correction of a corneal ablation profile that is attended by acceptable computational outlay and does not include a fundamental limitation to the compensation of specific disturbing effects specified in advance.

In achieving this object, the invention proceeds from a method for determining control information for controlling laser radiation irradiated onto the cornea of an eye, to be treated photorefractively, during this method a corneal ablation profile obtained by measuring the optical properties of the eye to be treated being corrected with the aid of correction information, and the control information being formed on the basis of the corrected ablation profile thus produced.

It is provided in this case according to the invention that the ablation profile is transformed into a spatial frequency spectrum, in that a corrected amplitude value is then determined in each case for various discrete spectral components of the ablation profile on the basis of stored amplitude correction information, and in that subsequently the spatial frequency spectrum with the amplitude corrected spectral components is backtransformed into the geometric spatial region in order to determine the corrected ablation profile, the amplitude correction information respectively representing for a number of spatial frequencies differing at least by the frequency value a predetermined relationship between values of the amplitude at the relevant spatial frequency and corrected amplitude values at this spatial frequency.

The invention is not restricted solely to the amplitude correction of the spectral components of the spatial frequency spectrum. It can equally be applied for spectral phase correction. Consequently, in the case of a method of the generic type it can be provided as an alternative or in addition that the ablation profile is transformed into a spatial frequency spectrum, in that a corrected phase value is then determined in each case for various discrete spectral components of the ablation profile on the basis of stored phase correction information, and in that subsequently the spatial frequency spectrum with the phase corrected spectral components is backtransformed into the geometric spatial region in order to determine the corrected ablation profile, the phase correction information respectively representing for a number of spatial frequencies differing at least by the frequency value a predetermined relationship between values of the phase at the relevant spatial frequency and corrected phase values at this spatial frequency.

Alternatively or in addition to the amplitude and phase corrections, the invention can correct the real part or/and the imaginary part of one or more spectral components of the spatial frequency spectrum (in the event of complex representation). Consequently, it is possible according to the invention to determine a corrected real part value or a corrected imaginary part in each case for various discrete spectral components of the ablation profile on the basis of stored real part or/and imaginary part correction information. Subsequently the spatial frequency spectrum with the real part or/and the imaginary part corrected spectral components is backtransformed into the geometric spatial region in order to determine the corrected ablation profile. In this case, the real part correction information respectively represent for a number of spatial frequencies differing at least by the frequency value a predetermined relationship between values of the real part at the relevant spatial frequency and corrected real part values at this spatial frequency. The imaginary part correction information represent corresponding relationships for the spectral imaginary part.

Thus, in accordance with the invention one or more parameters (amplitude, phase, real part, imaginary part) of various discrete spectral components of the spatial frequency spectrum are corrected with the aid of relationships determined empirically in advance. Only the parameters of amplitude and phase are expressly mentioned below, but it goes without saying that the relevant statements can be transferred equally to real part and imaginary part of the spectral components.

The invention is based on the observation that various spatial frequency components inside an ablation profile are transferred in different form to the cornea. Some spectral components of the ablation profile are to be found again in the actual removal profile in a more or less strongly attenuated fashion, while others are to be found substantially unattenuated or, in some circumstances, even in amplified fashion. However, it is not only the amplitude of the spectral components that can change upon the transfer of the removal profile into the cornea—so, too, can the phase. These amplitude and phase changes can be taken into account with the aid of the amplitude- and phase-related functional relationships represented by the correction information. In this case, an amplitude or/and phase corrected spectral component can respectively be determined with the aid of these relationships for a multiplicity of discrete spectral components of the ablation profile. Backtransformation of the spectrum with the amplitude or/and phase corrected spectral components into the spatial region delivers a corrected ablation profile that leads with good accuracy to the desired ablation profile after operation and after concluded wound healing and other postoperative transitional processes.

The amplitude or/and phase correction information are preferably produced in a way such that a multiplicity of desired ablation profiles and a multiplicity of associated actual ablation profiles are respectively transformed into a spatial frequency spectrum, in that with the aid of the desired and the actual spatial frequency spectra for a number of discrete spatial frequencies differing with regard to frequency value or/and spatial direction a functional relationship is respectively determined for the dependence of the actual amplitude or/and the actual phase at the relevant spatial frequency on the desired amplitude or/and the desired phase at this spatial frequency, and in that the amplitude or/and phase correction information of data are formed that describe the functional relationships determined.

By contrast with the mode of procedure in accordance with US 2005/107775 A1, this method does not have recourse to a predefined transmission model, but respectively individually determines an amplitude-related or/and a phase-related transmission function with the aid of an existing database of desired ablation profiles and associated actual ablation profiles for various discrete spatial frequencies. A Butterworth lowpass is used as transmission model in US 2005/107775 A1. This model is independent of amplitude and phase; for each spatial frequency, the ablation profile, obtained by measurement, of a patient is weighted with an amplitude- and phase-independent factor, dependent only on the relevant frequency value. By contrast, the inventive approach remedies the restriction to amplitude- and phase-independent weighting factors. If the available database expresses a nonlinear dependence of the actual amplitude on the desired one, or of the actual phase on the desired one for one or more spatial frequencies, this can be reflected by the functional relationships.

Moreover, the inventive mode of procedure allows the consideration of frequency couplings, a point of view not considered in US 2005/107775 A1. It has been shown with the aid of experiments that the amplitude or/and phase transmission function at one spatial frequency can also depend on the amplitude or phase at one or more other spatial frequencies. To express this differently, the various spectral components of a desired ablation profile can exert a mutual influence on the actual ablation profile arising postoperatively. It is therefore to be recommended during the determination of the functional relationships to examine the dependence of the actual amplitude or/and the actual phase of at least one spatial frequency on the desired amplitude or/and the desired phase of at least one other spatial frequency in such a way that at least a portion of the functional relationships specifies the actual amplitude or/and the actual phase at the respectively relevant spatial frequency also as a function of the desired amplitude or/and the desired phase at least one other spatial frequency.

The amplitude or/and phase correction information can be implemented in various ways. One possibility consists in a tabular representation, another in a representation in the form of one or more mathematical formulas. The amplitude or/and phase correction information can supply the corrected amplitude and phase values directly as output. Alternatively, the amplitude or/and phase correction information can supply as output only correction values with which the spectral components of the ablation profile has still to be combined multiplicatively or additively.

In accordance with one embodiment, various spectral components of the ablation profile can be corrected individually on the basis of a respectively assigned functional relationship. In the case of a spatial frequency spectrum dependent on spatial direction, it is, in particular, possible in addition that spectral components of the same frequency value but different spatial direction are corrected differently. A very fine correction of the ablation profile resolved in terms of frequency and spatial direction is possible in this way. If required, the correction information can even comprise, for all spectral components of the spatial frequency spectrum of the ablation profile, one amplitude-related functional relationship each or/and one phase-related functional relationship each for the spectral amplitude or/and phase, in order to permit individual correction of all the spectral components.

It is likewise conceivable to determine for a group of spectral components of the same frequency value but different spatial direction of the ablation profile a common amplitude or/and phase corrected spectral component on the basis of the amplitude or/and phase correction information. In the case of this variant, individual spectral components of the same frequency value are not corrected differently. Instead of this, a common amplitude or/and phase corrected spectral component is determined that is equal for all spatial directions of the group. For example, to this end amplitudes or/and phases of the spectral components of the group can be averaged, and the common amplitude or/and phase corrected spectral component can be determined as a function of the amplitude or/and phase mean value.

If possible frequency couplings have been considered when determining the correction information, at least one of the relationships represented by the amplitude correction information can specify the corrected amplitude values at the relevant spatial frequency also as a function of the value of the amplitude at least one other spatial frequency. Likewise, at least one of the relationships represented by the phase correction information can specify the corrected phase values at the relevant spatial frequency also as a function of the value of the phase at least one other spatial frequency.

Fourier transformation is to be recommended for the spectral transformation of the ablation profile of an eye to be treated. Discrete Fourier transformation suffices for discrete frequency representation of the spatial frequency spectrum of the ablation profile, it being possible to have recourse to methods of fast discrete Fourier transformation for the purpose of high computational efficiency. Consequently, inverse discrete Fourier transformation, in particular fast inverse discrete Fourier transformation, can be used for the backtransformation of the corrected spatial frequency spectrum. The Fourier transformation and its inverse process are current methods amongst experts for determining a frequency spectrum (in particular a discrete frequency spectrum) from a temporal or spatial signal (the ablation profile of the eye to be treated actually constitutes a two-dimensional spatial signal). It is therefore possible to dispense here with explaining the basic mathematics of Fourier transformation and its inversion.

Complex Fourier analysis in complex numerical space is to be recommended in particular for separately determining the amplitude and phase of the various spectral components of the spatial frequency spectrum of the ablation profile. The mathematical principles relating to this are also long-known to those skilled in the art concerned.

It goes without saying that Fourier analysis is not the sole method of the spectral examination of the ablation profile. Other spatial frequency transformations are also conceivable, of course. Reference may be made purely by way of example to discrete cosine transformation, which approximates a spatial signal by cosine series.

BRIEF DESCRIPTION OF THE DRAWINGS

The invention is explained in further detail below with the aid of the attached drawings, in which.

DETAILED DESCRIPTION

Figure 1:
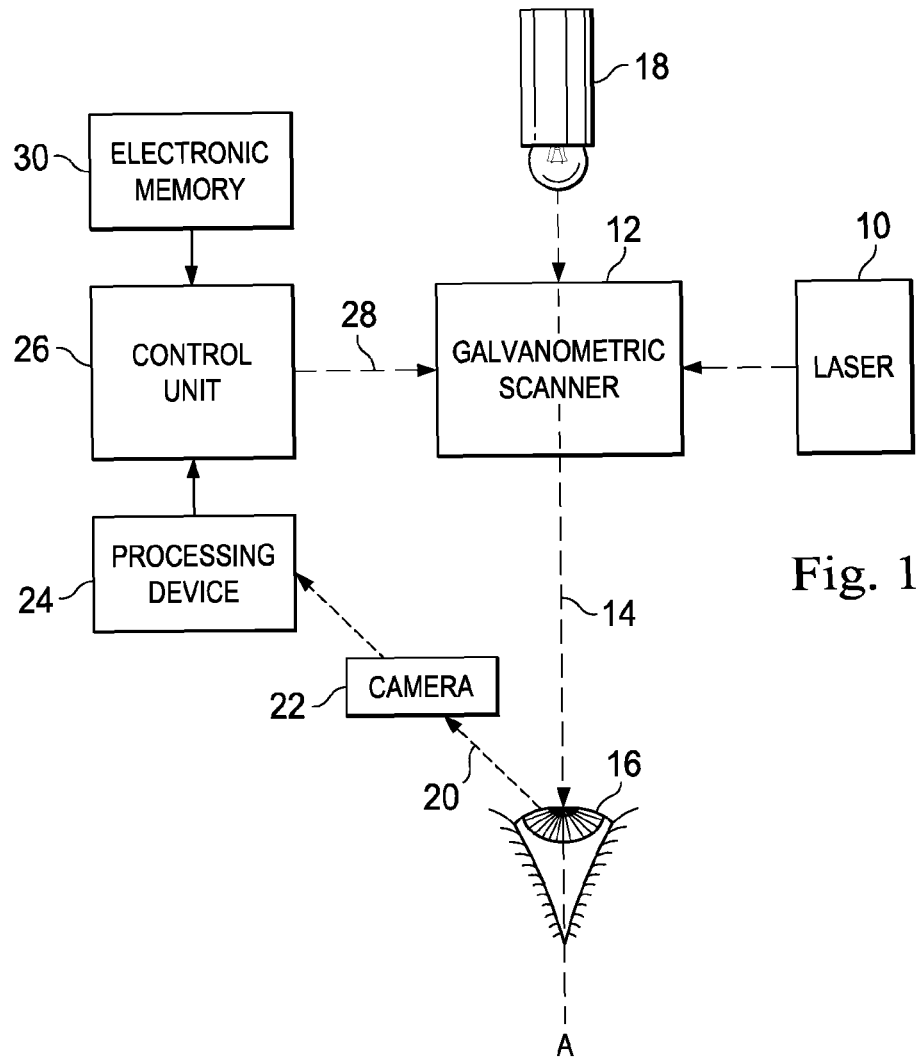
FIG. 1 shows a schematic of an exemplary embodiment of a device for carrying out photorefractive corneal surgery of the eye.

The device shown in FIG. 1 for carrying out photorefractive corneal treatment comprises a laser 10 that supplies the laser radiation required for the photoablation. The photoablation can be carried out on the corneal surface or/and intrastromally, that is to say in the corneal stroma. An excimer laser with an emission wavelength of 193 nm, for example, particularly comes into consideration as laser 10 for the photoablation. Alternatively, it is possible, for example, to use an Er:YAG solid state laser with an emission wavelength of 2.94 μm, or a UV solid state laser (for example Nd:YAG with 213 nm).

The laser radiation is deflected by means of a galvanometric scanner 12; the deflected laser beam—denoted by 14—is subsequently directed onto the cornea of an eye 16 to be treated. A further beam is directed onto the eye 16 in a fashion coaxial with the laser beam 14. This further beam originates from a so-called positioning light source 18 and defines a reference axis A that is stationary in space.

During the operation, the eye 16 generally moves relative to the axis A. The eye is illuminated with infrared radiation—in a way not illustrated in more detail—in order to track the processing beam 14 during such eye movements. The imaging radiation denoted by 20 generates in a CCD or CMOS camera 22 images that are electronically processed in a downstream image processing device 24. The result of the image processing is input into an arithmetic and control unit 26 that takes over the image evaluation and the control of the scanner 12. The arithmetic and control unit 26 outputs a suitable actuating signal 28 to the scanner 12 for this purpose. This actuating signal directs the processing beam 14 in such a way that an ablation profile previously determined for the eye 16 to be treated is processed. The optical errors of the eye 16 can thus be corrected by photoablation of corneal tissue. The ablation profile processed for the above purpose is a corrected ablation profile resulting from an original ablation profile obtained by measuring the optical properties of the eye 16, and from a subsequent correction of the ablation profile.

The original ablation profile can be determined, for example, from a spatially resolved measurement of the wavefront aberration of the eye 16 by means of a video aberroscope (not illustrated in more detail). Reference is made to DE 100 22 995 C2 for more detail on such wavefront aberration measurement and on the determination of an ablation profile from the measured wavefront aberration irregularity. The arithmetic and control unit 26 can be set up for the purpose of carrying out the computing operations required for calculating the wavefront aberration irregularity and the ablation profile. It is likewise possible for the original ablation profile to be obtained by means of a separate measuring and computing arrangement and for only the finished ablation profile to be fed to the arithmetic and control unit 26.

An electronic memory 30 contains the correction information required for correcting the original ablation profile determined from the wavefront aberration measurement. The correction is necessary because the ablation profile resulting postoperatively generally deviates from the theoretical desired ablation profile obtained by optical measurement of the eye 16. The deviations can have various causes. For one thing, the postoperative course of wound healing can lead to changes in the cornea. For example, epithelial smoothing can give rise to a lowpass filter effect as explained in US 2005/107775 A1. The course of wound healing can depend not only on the biological, in particular tissue-problems properties of the respective patient, but also on the laser system used. Optical losses during laser treatment, in particular reflection losses, may be named as further parameters that can lead to deviation from the desired ablation profile of the actual ablation profile that finally results.

Generally valid data or algorithms for correcting the desired ablation profile are not possible as a rule, because of the multiplicity of different disturbing factors that, in addition, can differ from laser system to laser system and from patient to patient. Rather, it is necessary to determine appropriate correction information empirically (experimentally) for the laser system respectively used, the required database comprising the desired and actual ablation profiles of a multiplicity of patients treated with the relevant laser system. It goes without saying that the database can be updated with the data of more recent patients continually or at regular intervals, in order to adapt the correction information if necessary.

The correction information stored in the memory 30 represent correction functions for the spectral amplitude or/and phase for a number of different discrete spatial frequencies. For the sake of clarity, only the spectral amplitude correction will be examined below, whereas the phase correction will not be fully explained. However, it may be pointed out expressly that the remarks relating to amplitude correction are valid correspondingly for spectral phase correction.

The amplitude correction functions represented by the correction information represent an empirically determined relationship between the amplitude of various spectral components of the postoperatively resulting ablation profile (actual amplitude) and the amplitude of the corresponding spectral components of the desired ablation profile (desired amplitude) obtained by optical measurement of the eye 16. Each of these relationships describes the functional dependence of the actual amplitude at a specific spatial frequency at least as a function of the desired amplitude at this spatial frequency. In one possible development, at least some of the amplitude correction functions can also describe the actual amplitude of the relevant spatial frequency as a function of the desired amplitude at one or more other spatial frequencies. Frequency couplings can be considered in this way when the desired ablation profile is being transmitted into the actual profile.

Figure 2:
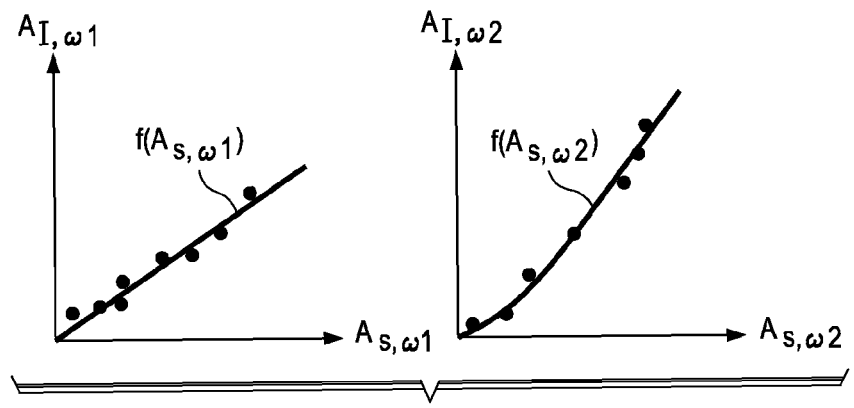
FIG. 2 shows examples of fitting functions for the functional representation of the spectral amplitude transmission response in the case of corneal treatment for various spatial frequencies.

The mode of procedure during the determination of the amplitude correction functions will now be explained with reference to FIG. 2. There are shown there two exemplary diagrams that include for two different spatial frequencies $\omega_1$, $\omega_2$ the value pairs of actual amplitude and desired amplitude of a multiplicity of patients at the relevant spatial frequency $\omega_1$ and $\omega_2$, respectively. Each value pair is indicated in the diagrams by a point. $A_{S, \psi 1}$ and $A_{S, \omega 2}$ in this case denote the desired amplitude at the frequency $\omega_1$ and $\omega_2$, respectively, whereas $A_{1, \omega 1}$ and $A_{1, \omega 2}$ specify the actual amplitude at the relevant frequency. The desired and actual amplitudes are obtained by transforming the preoperative desired ablation profile and the postoperative actual ablation profile of each individual patient of the database into the spatial frequency region and reading the amplitude value from the two spectra at the corresponding spectral line. The spectral transformation into the spatial frequency region is preferably performed by means of discrete Fourier transformation. This yields for each ablation profile a spatial frequency spectrum in the form of a matrix whose matrix elements specify the amplitude of a respective spectral line of the spectrum. (A phase line spectrum can additionally be determined when the complex Fourier transformation is applied.) The various discrete spectral lines of the spatial frequency spectrum are determined by frequency value and spatial direction. Since the ablation profile is a two-dimensional profile which can be represented in an X,Y coordinate system, the spatial frequencies obtained in the ablation profile can have a different amplitude or/and phase as a function of spatial direction.

Thus, two amplitude line spectra, specifically the actual spectrum and the desired spectrum, are obtained from the database for each patient.

Thus, a collection of value pairs of spectral desired amplitude and spectral actual amplitude is made available by the desired and actual spectra of the various patients of the database at the respectively relevant spatial frequency for each of a number of spatial frequencies differing with regard to frequency value or/and spatial direction. Each of the value pairs originates in this case from one of the patients. Such a collection is respectively represented by the points in the two diagrams of FIG. 2.

Attempt is now made in a subsequent phase to give a functional description of the dependence of the actual amplitude on the desired amplitude at the relevant spatial frequency. This is performed in a so-called fitting method in which the distribution of the various value pairs is approximated with the aid of a fitting function. Two different examples of such a fitting function are shown in FIG. 2. The left-hand diagram is a linear fitting function (denoted by $f(A_{S, \omega 1})$), whereas the right-hand diagram shows a nonlinear fitting function, specifically in concrete terms a quadratic fitting function (denoted by $f(A_{S, \omega 2})$). It goes without saying that completely different types of fitting functions can be used depending on the distribution of the value pairs of actual amplitude and desired amplitude. Linear and quadratic fitting functions are only to be regarded purely as examples; any other desired nonlinear fitting functions can equally be used.

Such fitting functions are determined for a multiplicity of spatial frequencies. A separate fitting function can be determined for each spectral line, in principle. It is thus possible also to assign a dedicated fitting function to spectral lines of equal frequency value but different spatial direction.

In accordance with a divergent embodiment, at least a portion of the spectral lines are combined in groupwise fashion, each group containing spectral lines of equal (or at least approximately equal) frequency value, but different spatial direction. In this process, the value pairs of desired amplitude and actual amplitude of each individual patient are averaged over the various spectral lines of the group, and a search is made for a fitting function for the averaged value pairs. If use is made of Fourier transformation as spectral transformation, and the center of the resulting spectral matrices of the spatial frequency is assigned to zero, spectral lines of equal frequency value but different spatial direction can be found in rings around the center of the matrix. A common fitting function can be determined for each such frequency ring.

The arithmetic and control unit 26 can be set up to determine the fitting functions and, if desired, also to carry out the spectral transformation of the ablation profiles of the database. However, at least a portion of these computing operations can also be carried out in advance by a separate arithmetic unit. In any event, suitable data that describe the fitting functions are stored in the memory 30. This can be in the form of an algorithm or in tabular form. It is advantageous when using the fitting functions that there is no need to stipulate a specific transmission model in advance, something which would mean being restricted to specific disturbing effects. Irrespective of the particular type of disturbing effects that occur, the fitting functions can be used to achieve good modeling of the actual transmission response from desired ablation profile to actual ablation profile.

Reference is now made to FIG. 1 again. For the purpose of successful treatment of the eye 16, the arithmetic and control unit 26 determines a corrected ablation profile from the desired ablation profile obtained by optical measurement of the eye 16, doing so with the aid of the fitting functions stored in the memory 30, and controls the scanner 12 in accordance with this corrected profile. In order to correct the desired ablation profile, the arithmetic and control unit 26 carries out a spectral transformation of the desired ablation profile in the spatial frequency region, and thus obtains a desired spatial frequency spectrum for the eye 16. Subsequently, the arithmetic and control unit 26 determines corrected amplitude values for at least a portion of the spectral components of the spatial frequency spectrum with the aid of the fitting functions stored in the memory 30. (Alternatively or in addition, the arithmetic and control unit 26 can determine corrected phase values for at least a portion of the spectral components.) The arithmetic and control unit 26 then uses the corrected amplitude values to form a corrected spatial frequency spectrum, and transforms the latter back into the geometric spatial region. The result is the corrected ablation profile, which is adopted as the basis for controlling the scanner 12.

During the spectral amplitude correction of the ablation profile, each spectral component of the spatial frequency spectrum, which is preferably present in the form of a matrix, can be corrected individually with the aid of a respective fitting function. As previously explained, individual fitting functions can respectively be assigned in common to a group of spatial frequencies. Consequently, the spectral correction of the ablation profile can also be performed in groupwise fashion by averaging amplitudes of groups of spectral components of equal frequency value but having a different spatial direction of the ablation profile, and the amplitude mean value thus determined is corrected with the aid of a fitting function assigned to the relevant group. In such a mode of procedure, all the spectral components of the group are assigned the same corrected amplitude value.

Figure 3:
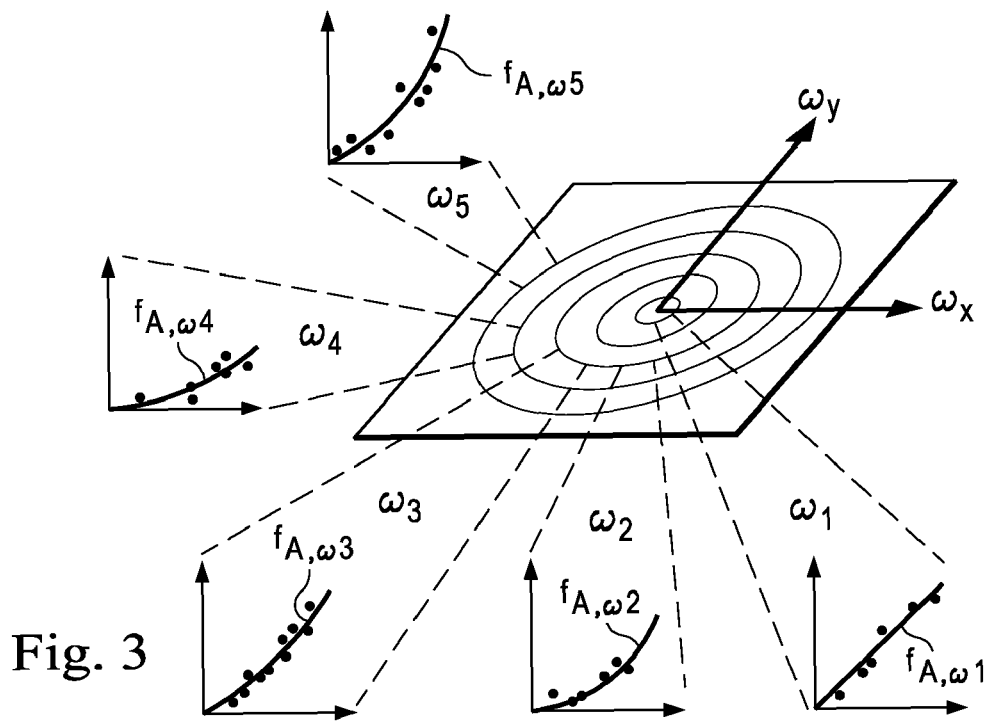
FIG. 3 shows a schematic for the purpose of illustrating a groupwise amplitude correction of the spectral components of a corneal ablation profile.
Figure 4:
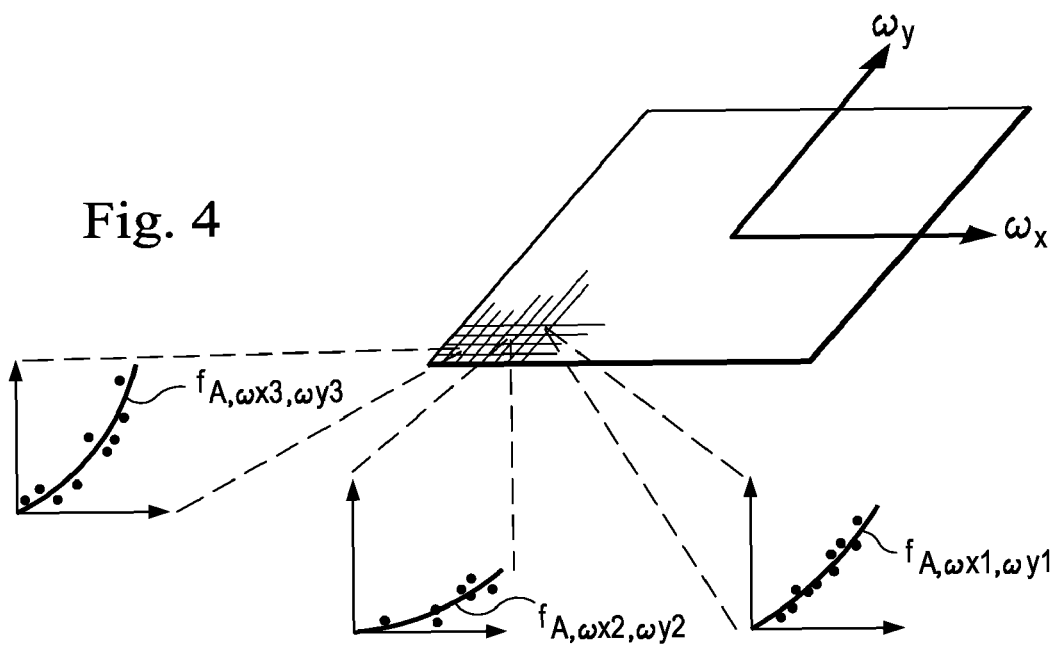
FIG. 4 shows a schematic for the purpose of illustrating an individual correction of the spectral components of a corneal ablation profile.

The two different modes of procedure outlined above are explained once again in pictorial fashion in FIGS. 3 and 4. FIG. 3 shows the case of a groupwise correction of spectral components of the ablation profile, while FIG. 4 shows the case of an individual correction. It goes without saying that the two methods can be combined with one another by correcting individual spectral lines individually for amplitude, and others, by contrast, in groupwise fashion.

FIG. 3 indicates five different frequency rings that represent locations of equal frequency value in the two-dimensional spatial frequency domain defined by orthogonal spatial frequency components $\omega_x$ and $\omega_y$. These frequency rings are characterized by frequency values $\omega_1$, $\omega_2$, $\omega_3$, $\omega_4$, $\omega_5$. Each frequency ring is assigned a separate amplitude correction function $f_{A, \omega 1}$ to $F_{A, \omega 5}$, with the aid of which an amplitude mean value determined for the spectral lines of the relevant frequency ring is corrected. The correction is formed simply in such a way that the relevant (average) spectral amplitude value of the ablation profile of the eye 16 is taken as actual amplitude value, and the desired amplitude value required to attain this actual amplitude value is determined with the aid of the associated fitting function.

By contrast, in FIG. 4 a separate fitting function is respectively assigned individually to various spectral components, frequency value and spatial direction of the individual spectral components being defined by the respective values of the spatial frequency components $\omega_x$, $\omega_y$. Etched by way of example are (nonlinear) fitting functions $f_{A, \omega x1, \omega y1}$ to $f_{A, \omega x3, \omega y3}$ that are assigned to spectral components with the spatial frequencies defined by the pairs $(\omega_{x1}, \omega_{y1})$, $(\omega_{x2}, \omega_{y2})$, $(\omega_{x3}, \omega_{y3})$. It has already been pointed out that there can occur between various spatial frequencies of the desired ablation profile frequency couplings which cause the actual amplitude at a spatial frequency to depend not only on the desired amplitude at this spatial frequency, but also on the desired amplitude at one or more other spatial frequencies. It is to be recommended to reflect such frequency couplings in the fitting functions for the purpose of correcting the ablation profile of an eye to be treated as accurately as possible. Consequently, it is preferred for the purpose of determining the fitting functions to consider not only pairs of desired amplitude and actual amplitude of one and the same spatial frequency, but tuples that are composed of the actual amplitude of a spatial frequency, the desired amplitude of this spatial frequency and the desired amplitude of one or more other spatial frequencies. This leads correspondingly to multidimensional fitting functions.

It has emerged that frequency couplings are noticeable through a relatively high scattering of the value pairs of actual amplitude and desired amplitude at a given spatial frequency. In accordance with one embodiment, in order to establish the extent of the frequency couplings it is possible firstly to carry out a correlation analysis of the actual amplitudes and desired amplitudes present in the patient database. For example, for this purpose it is possible to calculate the cross correlation of the actual amplitudes of various patients at one spatial frequency, and the desired amplitudes of the same patient at this spatial frequency and a number of other spatial frequencies. The result is a cross correlation matrix from which it may be seen how strongly the actual amplitude at one relevant spatial frequency is influenced by the desired amplitudes of the other spatial frequencies. If a strong influence on the part of one or more other spatial frequencies is established thereby, this influence can be considered by appropriate consideration of the desired amplitudes of these other spatial frequencies during function fitting. If, by contrast, the correlation analysis shows that the influence of the other spatial frequencies is slight or negligible, a one-dimensional function fitting can be carried out, as explained further above in conjunction with FIG. 2.

What is claimed is:

1. A method of controlling laser radiation irradiated onto a cornea of an eye to be treated photorefractively, the method comprising:
   obtaining a corneal ablation profile by measuring optical properties of an eye to be treated;
   transforming the corneal ablation profile into a spatial frequency spectrum;
   correcting an amplitude value for each of a plurality of discrete spectral components of the corneal ablation profile on the basis of stored amplitude correction information, wherein the stored amplitude correction information comprises a predetermined relationship between an amplitude value of a spatial frequency and a corrected amplitude value of the spatial frequency for a plurality of spacial frequencies;
   transforming the spatial frequency spectrum into a geometric spatial domain to obtain a corrected ablation profile utilizing the corrected amplitude values for each of the plurality of discrete spectral components; and
   controlling a laser source producing laser radiation irradiated onto the cornea of an eye with control information formed on the basis of the corrected ablation profile.

2. The method of claim 1, further comprising:
   determining for each of the plurality of discrete spectral components an amplitude-corrected spectral component on the basis of the amplitude correction information, where each of the plurality of discrete spectral components differs with respect to at least one of a frequency value and a spatial direction.

3. The method of claim 1, wherein at least one of the predetermined relationships represented by the amplitude correction information specifies a corrected amplitude value for a particular spatial frequency as a function of an amplitude of at least one other spatial frequency.

4. The method of claim 1, further comprising:
   determining for at least one frequency grouping of the plurality of discrete spectral components having the same frequency value but different spatial directions a common amplitude-corrected spectral component on the basis of the amplitude correction information.

5. The method of claim 4, further comprising:
   averaging the amplitudes of the spectral components of the at least one frequency grouping to obtain an amplitude average value; and
   determining the common amplitude-corrected spectral component as a function of the amplitude average value.

6. The method of claim 1, wherein the step of transforming the corneal ablation profile comprises:
   transforming the corneal ablation profile using Fourier analysis.

7. The method of claim 6, wherein the Fourier analysis is a complex Fourier analysis.

8. The method of claim 1, further comprising:
   transforming a plurality of desired corneal ablation profiles into a plurality of desired spatial frequency spectra;
   transforming a plurality of actual corneal ablation profiles into a plurality of actual spatial frequency spectra;
   determining, for a plurality of discrete spatial frequencies and based on the desired and actual frequency spectra, a functional relationship between an actual amplitude at each of the plurality of discrete spatial frequencies and a desired amplitude at that spatial frequency, wherein the plurality of discrete spatial frequencies differ with regard to at least one of a frequency value and a spatial direction; and
   generating the stored amplitude correction information using data representative of the determined functional relationships.

9. The method of claim 8, further comprising:
   determining at least one of the functional relationships by linear or nonlinear approximation.

10. The method of claim 8, further comprising:
    examining a dependence of the actual amplitude of at least one of the plurality of discrete spatial frequencies on the desired amplitude of at least one other of the plurality of discrete spatial frequencies; and
    wherein the functional relationship specifies the actual amplitude of the at least one of the plurality of discrete spatial frequencies as a function of the desired amplitude of the at least one other of the plurality of discrete spatial frequencies.

11. A method of controlling laser radiation irradiated onto a cornea of an eye to be treated photorefractively, the method comprising:
    obtaining a corneal ablation profile by measuring optical properties of an eye to be treated;
    transforming the corneal ablation profile into a spatial frequency spectrum;
    correcting a phase value for each of a plurality of discrete spectral components of the corneal ablation profile on the basis of stored phase correction information, wherein the stored phase correction information comprises a predetermined relationship between a phase value of a spatial frequency and a corrected phase value of the spatial frequency for a plurality of spacial frequencies;
    transforming the spatial frequency spectrum into a geometric spatial domain to obtain a corrected ablation profile utilizing the corrected phase values for each of the plurality of discrete spectral components; and controlling a laser source producing laser radiation irradiated onto the cornea of an eye with control information formed on the basis of the corrected ablation profile.

12. The method of claim 11, further comprising:

determining for each of the plurality of discrete spectral components a phase-corrected spectral component on the basis of the phase correction information, where each of the plurality of discrete spectral components differs with respect to at least one of a frequency value and a spatial direction.

13. The method of claim 11, wherein at least one of the predetermined relationships represented by the phase correction information specifies a corrected phase value for a particular spatial frequency as a function of a phase of at least one other spatial frequency.

14. The method of claim 11, further comprising:

determining for at least one frequency grouping of the plurality of discrete spectral components having the same frequency value but different spatial directions a common phase-corrected spectral component on the basis of the phase correction information.

15. The method of claim 14, further comprising:

averaging the phases of the spectral components of the at least one frequency grouping to obtain a phase average value; and determining the common phase-corrected spectral component as a function of the phase average value.

16. The method of claim 11, wherein the step of transforming the ablation profile includes:

transforming the ablation profile using Fourier analysis.

17. The method of claim 16, wherein the Fourier analysis is a complex Fourier analysis.

18. The method of claim 11, further comprising:

transforming a plurality of desired corneal ablation profiles into a plurality of desired spatial frequency spectra;

transforming a plurality of actual corneal ablation profiles into a plurality of actual spatial frequency spectra;

determining, for a plurality of discrete spatial frequencies and based on the desired and actual frequency spectra, a functional relationship between an actual phase at each of the plurality of discrete spatial frequencies and a desired phase at that spatial frequency, wherein the plurality of discrete spatial frequencies differ with regard to at least one of a frequency value and a spatial direction; and generating the stored phase correction information using data representative of the determined functional relationships.

19. The method of claim 18, further comprising:

determining at least one of the functional relationships by linear or nonlinear approximation.

20. The method of claim 18, further comprising:

examining a dependence of the actual phase of at least one of the plurality of discrete spatial frequencies on the desired phase of at least one other of the plurality of discrete spatial frequencies; and wherein the functional relationship specifies the actual phase of the at least one of the plurality of discrete spatial frequencies as a function of the desired phase of the at least one other of the plurality of discrete spatial frequencies.

21. A method of controlling laser radiation irradiated onto a cornea of an eye to be treated photorefractively, the method comprising:

obtaining a corneal ablation profile by measuring optical properties of an eye to be treated;

transforming the corneal ablation profile into a spatial frequency spectrum;

correcting a real-part value of a complex valued magnitude for each of a plurality of discrete spectral components of the corneal ablation profile on the basis of stored real-part correction information, wherein the stored real-part correction information comprises a predetermined relationship between a real part-value of a spatial frequency and a corrected real-part value of the spatial frequency for a plurality of spacial frequencies;

transforming the spatial frequency spectrum into a geometric spatial domain to obtain a corrected ablation profile utilizing the corrected real-part values for each of the plurality of discrete spectral components; and controlling a laser source producing laser radiation irradiated onto the cornea of an eye with control information formed on the basis of the corrected ablation profile.

22. The method of claim 21, further comprising:

determining for each of the plurality of discrete spectral components a real-part-corrected spectral component on the basis of the real-part correction information, where each of the plurality of discrete spectral components differs with respect to at least one of a frequency value and a spatial direction.

23. The method of claim 21, wherein at least one of the predetermined relationships represented by the real-part correction information specifies a corrected real-part value for a particular spatial frequency as a function of a phase of at least one other spatial frequency.

24. The method of claim 21, further comprising:

determining for at least one frequency grouping of the plurality of discrete spectral components having the same frequency value but different spatial directions a common real-part-corrected spectral component on the basis of the real-part correction information.

25. The method of claim 24, further comprising:

averaging the real-part values of the spectral components of the at least one frequency grouping to obtain an average real-part value; and determining the common real-part-corrected spectral component as a function of the average real-part value.

26. The method of claim 21, wherein the step of transforming the ablation profile includes:

transforming the ablation profile using Fourier analysis.

27. The method of claim 26, wherein the Fourier analysis is a complex Fourier analysis.

28. The method of claim 21, further comprising:

transforming a plurality of desired corneal ablation profiles into a plurality of desired spatial frequency spectra;

transforming a plurality of actual corneal ablation profiles into a plurality of actual spatial frequency spectra;

determining, for a plurality of discrete spatial frequencies and based on the desired and actual frequency spectra, a functional relationship between an actual real-part value at each of the plurality of discrete spatial frequencies and a desired real-part value at that spatial frequency, wherein the plurality of discrete spatial frequencies differ with regard to at least one of a frequency value and a spatial direction; and generating the stored real-part correction information using data representative of the determined functional relationships.

29. The method of claim 28, further comprising:

determining at least one of the functional relationships by linear or nonlinear approximation.

30. The method of claim 28, further comprising:
examining a dependence of the actual real-part value of at least one of the plurality of discrete spatial frequencies on the desired real-part value of at least one other of the plurality of discrete spatial frequencies; and
wherein the functional relationship specifies the actual real-part value of the at least one of the plurality of discrete spatial frequencies as a function of the desired real-part value of the at least one other of the plurality of discrete spatial frequencies.

31. A method of controlling laser radiation irradiated onto a cornea of an eye to be treated photorefractively, the method comprising:
obtaining a corneal ablation profile by measuring optical properties of an eye to be treated;
transforming the corneal ablation profile into a spatial frequency spectrum;
correcting a imaginary-part value of a complex valued magnitude for each of a plurality of discrete spectral components of the corneal ablation profile on the basis of stored imaginary-part correction information, wherein the stored imaginary-part correction information comprises a predetermined relationship between a imaginary part-value of a spatial frequency and a corrected imaginary-part value of the spatial frequency for a plurality of spacial frequencies;
transforming the spatial frequency spectrum into a geometric spatial domain to obtain a corrected ablation profile utilizing the corrected imaginary-part values for each of the plurality of discrete spectral components; and
controlling a laser source producing laser radiation irradiated onto the cornea of an eye with control information formed on the basis of the corrected ablation profile.

32. The method of claim 31, further comprising:
determining for each of the plurality of discrete spectral components a imaginary-part-corrected spectral component on the basis of the imaginary-part correction information, where each of the plurality of discrete spectral components differs with respect to at least one of a frequency value and a spatial direction.

33. The method of claim 31, wherein at least one of the predetermined relationships represented by the imaginary-part correction information specifies a corrected imaginary-part value for a particular spatial frequency as a function of a phase of at least one other spatial frequency.

34. The method of claim 31, further comprising:
determining for at least one frequency grouping of the plurality of discrete spectral components having the same frequency value but different spatial directions a common imaginary-part-corrected spectral component on the basis of the imaginary-part correction information.

35. The method of claim 34, further comprising:
averaging the imaginary-part values of the spectral components of the at least one frequency grouping to obtain an average imaginary-part value; and
determining the common imaginary-part-corrected spectral component as a function of the average imaginary-part value.

36. The method of claim 31, wherein the step of transforming the ablation profile includes:
transforming the ablation profile using Fourier analysis.

37. The method of claim 36, wherein the Fourier analysis is a complex Fourier analysis.

38. The method of claim 31, further comprising:
transforming a plurality of desired corneal ablation profiles into a plurality of desired spatial frequency spectra;
transforming a plurality of actual corneal ablation profiles into a plurality of actual spatial frequency spectra;
determining, for a plurality of discrete spatial frequencies and based on the desired and actual frequency spectra, a functional relationship between an actual imaginary-part value at each of the plurality of discrete spatial frequencies and a desired imaginary-part value at that spatial frequency, wherein the plurality of discrete spatial frequencies differ with regard to at least one of a frequency value and a spatial direction; and
generating the stored imaginary-part correction information using data representative of the determined functional relationships.

39. The method of claim 38, further comprising:
determining at least one of the functional relationships by linear or nonlinear approximation.

40. The method of claim 38, further comprising:
examining a dependence of the actual imaginary-part value of at least one of the plurality of discrete spatial frequencies on the desired imaginary-part value of at least one other of the plurality of discrete spatial frequencies; and
wherein the functional relationship specifies the actual imaginary-part value of the at least one of the plurality of discrete spatial frequencies as a function of the desired imaginary-part value of the at least one other of the plurality of discrete spatial frequencies.

41. An apparatus for performing laser treatment of an eye, comprising:
a laser for providing laser radiation;
a scanner for moving the laser radiation across a corneal surface of an eye to be treated;
memory for storing correction information representing, in relation to each of a plurality of spatial frequencies, a predetermined relationship between values of at least one spectral parameter at the spatial frequency and corrected parameter values at the spatial frequency; and
a control unit for controlling operation of the scanner based on a corrected ablation profile, wherein the control unit calculates the corrected ablation profile based on a corneal ablation profile obtained by measuring optical properties of the eye and the correction information stored in the memory by:
transforming the corneal ablation profile into a spatial frequency spectrum;
determining, in relation to each of various discrete spectral components of the ablation profile, a corrected value for at least one spectral parameter based on the stored correction information; and
transforming the spatial frequency spectrum with the parameter-corrected spectral components into the geometric spatial domain to obtain the corrected ablation profile.

42. The apparatus of claim 41, wherein the spectral parameter includes at least one of a spectral amplitude, a spectral phase, a real part of a complex valued magnitude, and an imaginary part of a complex valued magnitude.

43. A method of laser treating an eye, comprising:
providing correction information representing, in relation to each of a plurality of spatial frequencies that differ by at least a frequency value, a predetermined relationship between values of at least one spectral parameter for the spatial frequency and corrected parameter values for the spatial frequency;
transforming a corneal ablation profile into a spatial frequency spectrum, the corneal ablation profile obtained by measuring optical properties of an eye to be treated;

determining, in relation to each of various discrete spectral components of the ablation profile, a corrected value for at least one spectral parameter based on the provided correction information;

transforming the spatial frequency spectrum with the parameter-corrected spectral components into a geometric spatial domain to obtain a corrected ablation profile; and controlling laser radiation across a corneal surface of the eye based on the corrected ablation profile.

44. The method of claim 43, wherein the spectral parameter includes at least one of a spectral amplitude, a spectral phase, a real part of a complex valued magnitude, and an imaginary part of a complex valued magnitude.

* * * * *